United States Patent [19]

Tam

[11] Patent Number: 4,506,327

[45] Date of Patent: Mar. 19, 1985

[54] LIMITED-ANGLE IMAGING USING MULTIPLE ENERGY SCANNING

[75] Inventor: Kwok C. Tam, Schenectady, N.Y.

[73] Assignee: General Electric Company, Schenectady, N.Y.

[21] Appl. No.: 323,856

[22] Filed: Nov. 23, 1981

[51] Int. Cl.$^3$ .......................... G06F 15/42; H04N 5/32
[52] U.S. Cl. .................................... 364/414; 358/111; 364/413; 378/5; 378/901
[58] Field of Search ....................... 364/413, 414, 415; 378/901, 5; 358/111

[56] References Cited

U.S. PATENT DOCUMENTS

| | | | |
|---|---|---|---|
| 3,848,130 | 11/1974 | Macovski | 364/414 X |
| 3,971,948 | 7/1976 | Pfeiler et al. | 378/5 |
| 4,138,721 | 2/1979 | Boyd | 364/414 |
| 4,445,226 | 4/1984 | Brody | 378/99 |

FOREIGN PATENT DOCUMENTS

| | | | |
|---|---|---|---|
| 0037039 | 10/1981 | United Kingdom | 364/413 |
| 2098425 | 4/1982 | United Kingdom | 358/111 |

OTHER PUBLICATIONS

Tam, K. C. et al., "Limits to Image Reconstruction from Restricted Angular Input", IEEE Transactions on Nuclear Science, NS-28, (Feb. 1981), 179-183.

Tam, K. C. et al., "Tomographical Imaging with Limited-Angle Input", J. Opt. Soc. Am., vol. 71, No. 5, (May 1981), 582-592.

Tam, K. C. et al., "Limited-Angle Three-Dimensional Reconstructions Using Fourier Transform Iterations and Radon Transform Iterations", Optical Engineering, vol. 20, No. 4, (Jul./Aug. 1981), 586-589.

Riederer, S. J. et al., "Selective Iodine Imaging Using K-edge Energies in Computerized X-ray Tomography", Medical Physics, vol. 4, (1977), 474-481.

Inouye, T., "Image Reconstruction with Limited Angle Projection Data", IEEE Transactions on Nuclear Science, NS-26, (1979), 2666-2669.

Tam, K. C. et al., "3-D Object Reconstruction in Emission and Transmission Tomography with Limited Angular Input", IEEE Transactions on Nuclear Science, NS-26, (1979), 2797-2805.

Lent, A. et al., "An Iterative Method for the Extrapolation of Band-Limited Functions", Technical Report MIPG35, Oct. 1979, State University of New York at Buffalo.

Primary Examiner—Errol A. Krass
Assistant Examiner—Kevin J. Teska
Attorney, Agent, or Firm—Donald R. Campbell; James C. Davis, Jr.; Paul R. Webb, II

[57] ABSTRACT

The fidelity of limited-angle x-ray computerized tomography imaging is improved by taking multiple scans using x-ray beams at different energies. The projection data of the composite object is decomposed into the projections of the individual component substances. Reconstruction of a single substance is done more accurately than reconstructing the composite object because more a priori information about the object, such as upper and lower bounds of the densities of the substances, is available. The reconstructed images of the components are superimposed to form an image of the composite object. The method is applicable to other imaging modalities.

4 Claims, 14 Drawing Figures

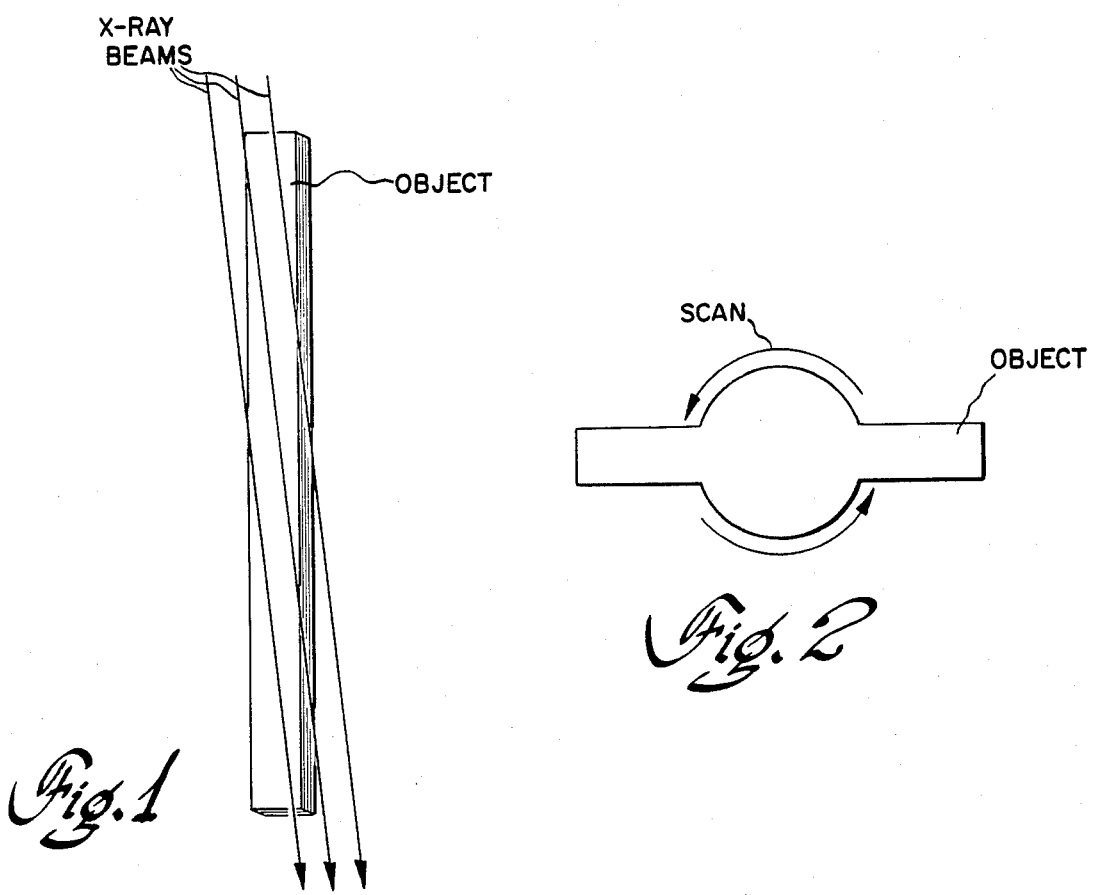
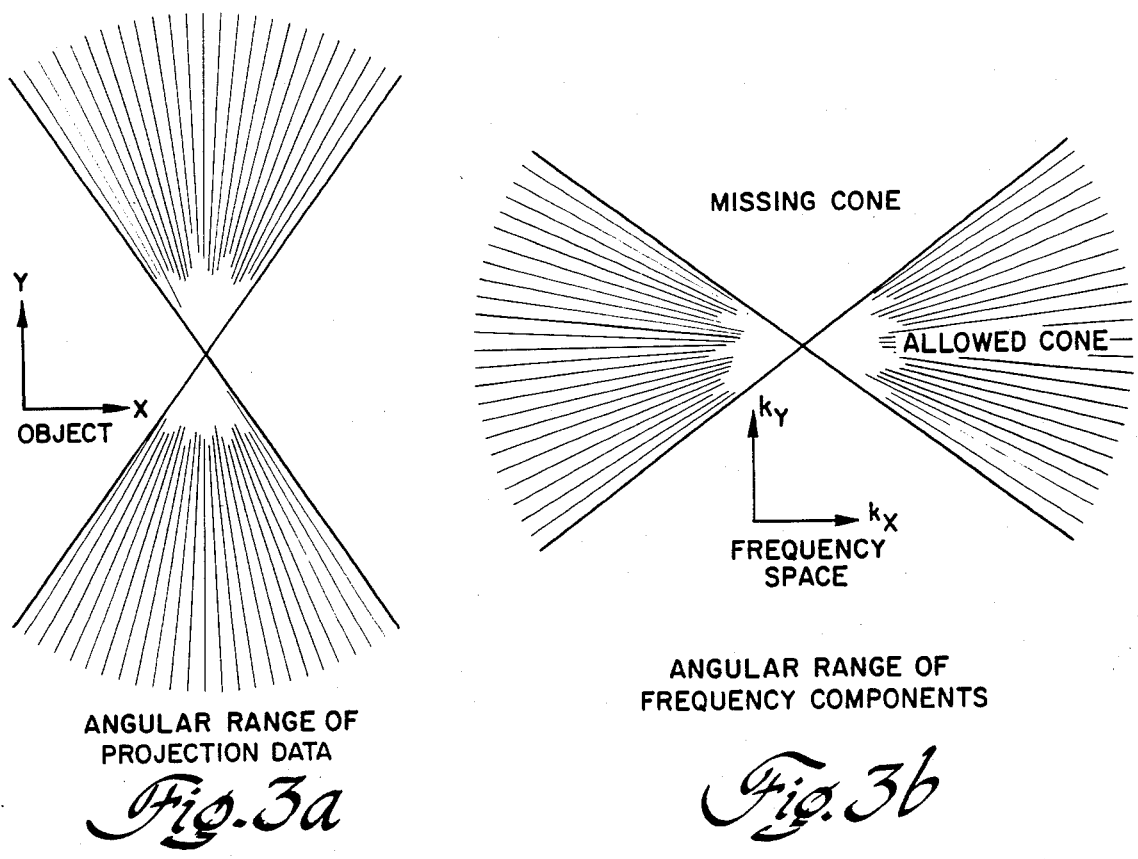

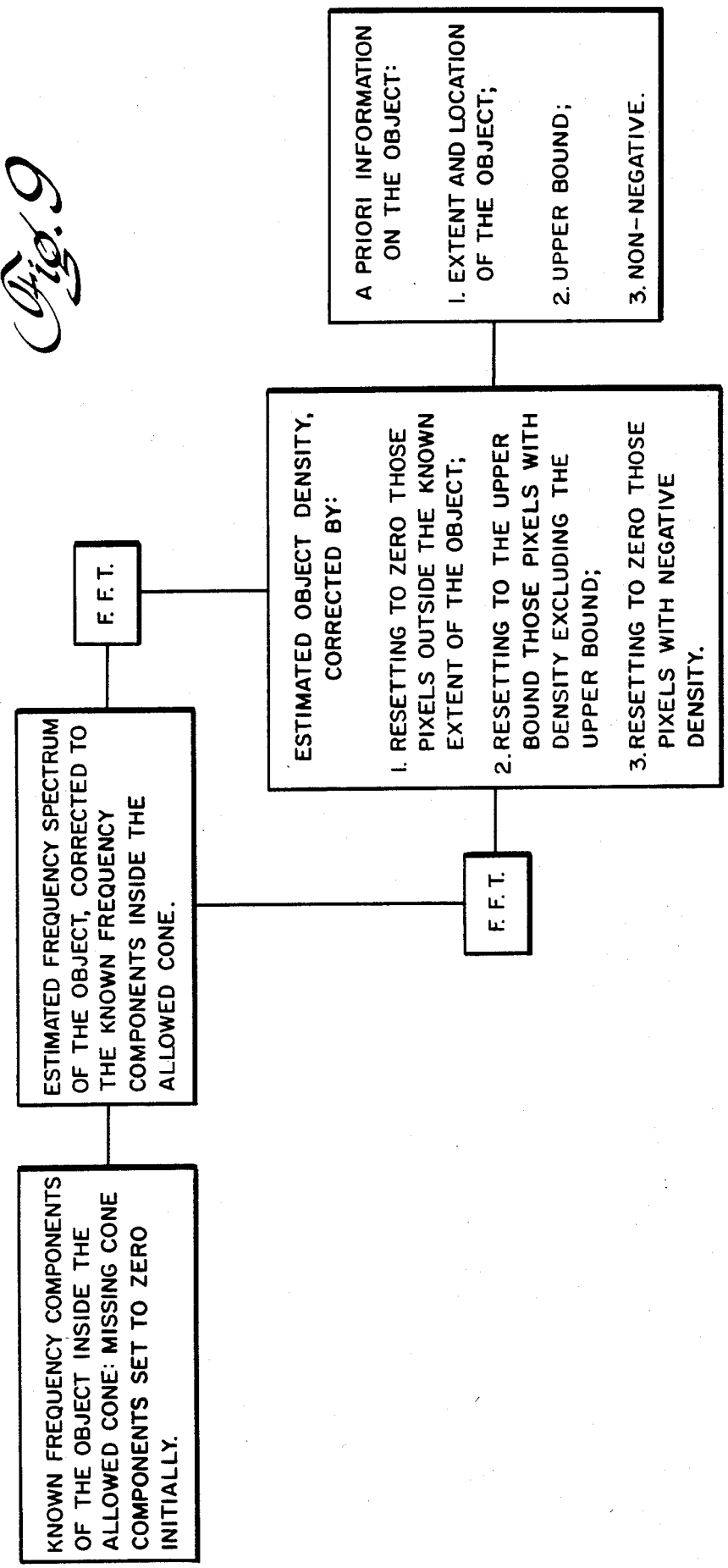

LIMITED-ANGLE IMAGING USING MULTIPLE ENERGY SCANNING

BACKGROUND OF THE INVENTION

This invention relates to computed tomography imaging and especially to the use of multispectral imaging in limited-angle reconstruction.

In some CT applications the object can be scanned only in a limited angular range. For instance, the industrial x-ray CT the object may be long and rectangular such that there is too much attenuation for x-ray beams at large oblique incidence angles, or the object might be obstructed in some angular range. These situations are illustrated in FIGS. 1 and 2. In electron microscopy biological specimens in the form of thin slices can only be scanned by electrons in a limited angular range because of strong attenuation of the electron beam at large oblique incidence angles.

There are many methods for reconstructing images from their projections. One of these is the Fourier method, which involves a transformation of the data from the projections into what is known as Fourier or frequency space. Points in the Fourier space for which there are no data are estimated by interpolation. The reconstruction is then obtained from the Fourier space by taking the inverse Fourier transform. FIG. 3a illustrates in the real, object space a limited angular range of projection data. It has been shown that from such restricted angular data one can calculate only the frequency components in a limited angular range in the frequency space, as illustrated in FIG. 3b. The region in the frequency space where the frequency components of an object are known are referred to as the "allowed cone" and where they are not known as the "missing cone".

In principle, the missing cone frequency components can be recovered and continued from those in the allowed cone through the knowledge of the location and finite extent of the object. There are several techniques for doing this, and in all of them the object is assumed to have finite boundaries and the density outside the boundary is set to zero. This a priori knowledge is coupled with the partial Fourier components in the allowed cone. For example, the frequency components of the object can be expanded in a Fourier series with the coefficients determined from the known extent of the object (see T. Inouye, IEEE Transactions on Nuclear Science, NS-26 (1979) 2666-2669). Another way to achieve this is through the iteration scheme proposed by the inventor, V. Perez-Mendez, and B. Macdonald, IEEE Transactions on Nuclear Science, NS-26 (1979) 2797-2805. The object is transformed back and forth between the object space and the frequency space, being corrected in each step by the finite object extent and the known frequency components. While it is theoretically possible to determine the object exactly, in practice recovery of the missing cone frequency components cannot be done perfectly because the problem is ill conditioned and because of errors in the input data and imprecision in numerical computation.

The principal object of the invention is to improve on this situation. Multiple energy scanning has been successfully used to enhance images in complete-angle scanning, in x-ray fluoroscopy imaging where a patient is imaged in conventional CT mode at different x-ray energies to separate out the iodine component in the image. Refer to S. J. Riederer and C. A. Mistretta, Medical Physics, 4 (1977) 474-481. The present invention is for limited-angle imaging and is distinguishable in other respects. The use of the upper and lower bounds of an object in limited-angle reconstruction has been proposed by A. Lent and H. Tuy, "An Iterative Method for the Extrapolation of Band-Limited Functions", Technical Report No. MIPG 35 (1979), State University of New York at Buffalo. Positivity, the constraint that physical objects have only non-negative density, is a particular case of the constraint of lower boundness. It was found by the inventor and V. Perez-Mendez, Optical Engineering, 20 (1981) 586-589 and other references, that incorporating the constraint of positivity in addition to the constraint of finite object extent produces only a small improvement in the limited-angle reconstruction of extended objects. This prior work on bounds is discussed in more detail later.

SUMMARY OF THE INVENTION

An improved method of limited-angle tomographic reconstruction for radiation imaging is realized by taking multiple scans of the composite object over a restricted angular range using an imaging agent (such as x-rays, electrons, neutrons, and ultrasound) at different energies. For an object composed of m substances, scanning is performed at m or greater energies. The substances have different transmission and attenuation characteristics with respect to the imaging agent and this property is used. The detected signals, which are projections of the composite object in the limited-angular range at different source energies, are fed into a computer. The composite object projections, given certain a priori information on the object, are decomposed into projections of each component substance. Reconstructed images of the individual substances are derived from the last-mentioned projections and known physical parameters of the object. The reconstructed images of the component substances are superimposed to form an image of the composite object.

One illustrative embodiment is an industrial x-ray CT imager. The projection data, given the number of substances and attenuation coefficients, is decomposed into projections of the component substances by solving linear equations. The reconstructed image of each substance is derived using a limited-angle reconstruction algorithm such as the Fourier transform iteration scheme proposed by the inventor, Perez-Mendez and Macdonald which is modified to reset to zero those pixels outside the known extent of the object, reset to the upper bound those pixels with density exceeding the upper bound, and reset to zero those pixels with negative density. By decomposing the object into its component substances the constraints of upper boundness and positivity are used more efficiently.

BRIEF DESCRIPTION OF THE DRAWINGS

FIG. 1 shows an object which is very long such that x-ray beams at small angles to the longitudinal direction are attenuated too much to serve any useful purpose;

FIG. 2 depicts an object with protrusions making it impossible to carry out complete-angle scanning;

FIGS. 3a and 3b are schematic representations of limited-angle information in object space and frequency space;

FIG. 9 is a flow chart of a limited-angle reconstruction method, a Fourier transform iteration scheme.

DESCRIPTION OF THE PREFERRED EMBODIMENTS

Figure 4A:
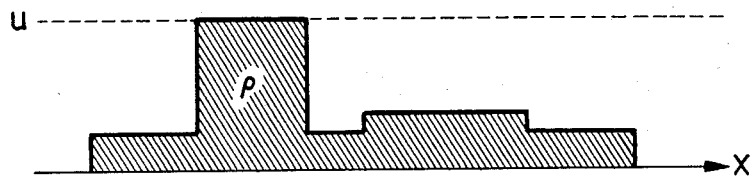
FIG. 4a is a cross section of a composite object made up of three component substances and shows the upper bound u of the density.
Figure 4B:
FIGS. 4b–4d are cross sections of the three components which have upper bounds $u_1$, $u_2$, and $u_3$.
Figure 4C:
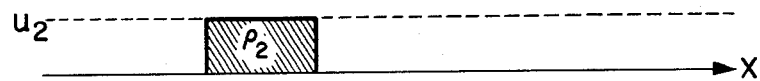
Figure 4D:

A method to improve the fidelity of reconstructed images in limited-angle x-ray CT imaging is realized by taking multiple scans of a composite object using x-ray beams at different energies. Individual component substances in the object which have different densities are separated out through the use of multiple energy scans. The rationale is that reconstructing a single substance can be done more accurately than reconstructing the composite object because there is more a priori or known information available. The method is applicable to any imaging modality in which the projection images of different substances in an object change in different ways under a change in the frequency or energy of the imaging agent (x-rays, electrons, neutrons, ultrasound, etc.). The component substances have different transmission properties and different attenuation coefficients with respect to the imaging agent; this property is used.

Assume an object is made of two component substances with density distributions $\rho_1(x,y)$ and $\rho_2(x,y)$. The object is scanned over the limited-angle by x-rays at energies $E_1$ and $E_2$, yielding composite projections $p(t,\theta,E_1)$ and $p(t,\theta,E_2)$ respectively ($t=$distance, $\theta=$scan angle). Let $\mu_i(E_j)$ represent the mass attenuation coefficient of $\rho_i(x,y)$ at x-ray energy $E_j$ ($i=1,2; j=1,2$) and let $p_i(t,\theta)$ represent the projection of $\rho_i(x,y)$, $i=1,2$. Then $p_1(t,\theta)$ is the first component substance projection and $p_2(t,\theta)$ is the second component substance projection, and we have:

$$p(t,\theta,E_1)=\mu_1(E_1)p_1(t,\theta)+\mu_1(E_1)p_2(t,\theta)$$
$$p(t,\theta,E_2)=\mu_1(E_2)p_2(t,\theta)+\mu_2(E_2)p_2(t,\theta) \quad (1)$$

From the linear equation system (1) one can solve for $p_1(t,\theta)$ and $p_2(t,\theta)$ from the measured quantities $p(t,\theta,E_1)$ and $p(t,\theta,E_2)$ and the known quantities $\mu_1(E_1)$, $\mu_1(E_2)$, $\mu_2(E_1)$, and $\mu_2(E_2)$. Then each of the density distributions $\rho_i(x,y)$ of the component substances can be reconstructed from the following information using a limited-angle reconstruction algorithm:

1. The component substance projection $p_i(t,\theta)$ in the limited-angular range,
2. The finite extent of the composite object, or that of $\rho_i(x,y)$,
3. The upper bound of $\rho_i(x,y)$, which is accurately known in general,
4. The lower bound of $\rho_i(x,y)$, preferably that there are only positive densities and no negative densities.

For an object composed of $m(>2)$ substances, x-ray scanning is performed at m or greater different energies; the scans are sequential or may be simultaneous. The reconstructed images of the individual component substances are superimposed to form a reconstruction of the composite object.

Multiple energy scanning is beneficial in limited-angle imaging because limited-angle reconstruction depends critically on the amount of a priori information available, and multiple energy scanning enables more a priori information to be utilized. Basically, the problem of image reconstruction is to generate an image consistent with all the given constraints. In complete-angle reconstruction, the constraints of projection data at all angles are sufficient to reconstruct the object uniquely (neglecting the effect of discrete angles for the time being). In limited-angle reconstruction, some of the projection data are missing, but they could be supplemented by the constraint of the finite object extent. However, the constraints of projection data and finite object extent are linear constraints. If only linear constraints are used, no real improvement in image quality can be expected by decomposing an object into component substances through multiple energy scanning and then reconstructing each component substance individually, because all the effects superimpose. (Note: The improvement obtained in selective iodine imaging mentioned above is basically enhancement of the iodine image by subtracting out the other unwanted component substances.) However, there is significant improvement when nonlinear constraints are used. Two nonlinear constraints which are useful for image reconstruction are upper-boundness and positivity.

Images reconstructed from the limited-angle information are not bounded by the upper and lower bounds as well as the finite spatial extent of the true object. The use of the bounds of the object in limited-angle reconstruction, without decomposing the composite object into its components has been proposed. How much improvement the use of an upper bound can bring about depends on how close the upper bound is to the object density everywhere. In general, no close upper bound for the composite object is available, whereas a close upper bound for a single substance is easily attainable. Thus reconstructing the individual component substances of the composite object utilizes the constraint of upper-boundness much more effectively than reconstructing the composite object itself does.

To illustrate the above statements, referring to FIGS. 4a–4d, consider an object $\rho(x,y)$ made of three component substances $\rho_1(x,y)$, $\rho_2(x,y)$, and $\rho_3(x,y)$ in the ratio 1:2:0.5, which have upper bounds u, $u_1$, $u_2$, and $u_3$. A cross section of the composite object and those of each component substance are illustrated. Two things are apparent from the figures. The upper bound u for the composite object matches $\rho(x,y)$ only in a small fraction of the region occupied by the object, whereas the upper bound $u_i$ of the density $\rho_i(x,y)$ of each individual component substance matches $\rho_i(x,y)$ throughout the region occupied by that component. Consequently, in limited-angle reconstruction the constraint of upper-boundness, i.e., resetting to the upper bound those pixels of the reconstructed image which have density values larger than the upper bound, would produce a much larger improvement in the reconstruction of the component $\rho_i(x,y)$ than in the case of the composite object $\rho(x,y)$.

Figure 5:
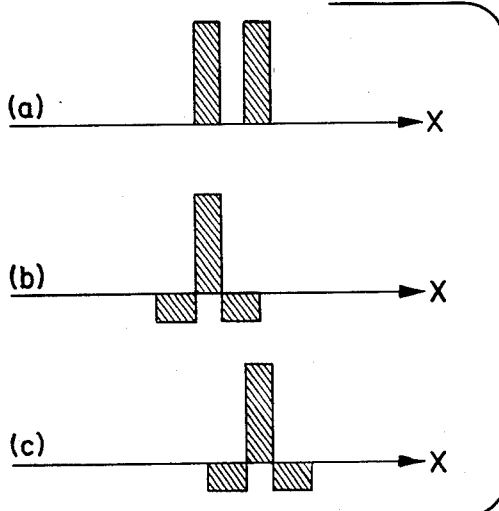
FIG. 5 is used to explain positivity and illustrates in (a) two objects and in (b) and (c) the same two objects with negative densities resulting from missing frequency components.

Positivity, the constraint that physical objects have only non-negative density, is a particular case of the constraint of lower-boundness. It was found that incorporating the constraint of positivity in addition to the constraint of finite object extent produces only little improvement in the limited-angle reconstructions of extended objects, assuming that the object is not decomposed into its component substances. The reason is that for an extended object, which can be thought of as a collection of a large number of point objects, the negative distortion of each of its point objects is superimposed on the positive densities and positive distortions of the other point objects, and thus does not show up as negative density or else is reduced in magnitude. Therefore, any attempt to apply the constraint of positivity in limited-angle reconstruction can only have little effect since not many negative densities appear in the distorted object. This is illustrated schematically in FIG. 5. In line (a) are two point objects and lines (b) and (c) represent the same two points with negative densities resulting from missing frequency components. The positive and negative densities overlap and partially cancel out; the result is that there is not much negative density.

When, however, each component substance of the composite object is reconstructed individually from limited-angle information, the positivity constraint is much more effective. This is because the negative distortion of any individual component substance is able to show up as negative density in the location occupied by other component substances in their absence. There are more negative densities to work with.

Figure 6A:
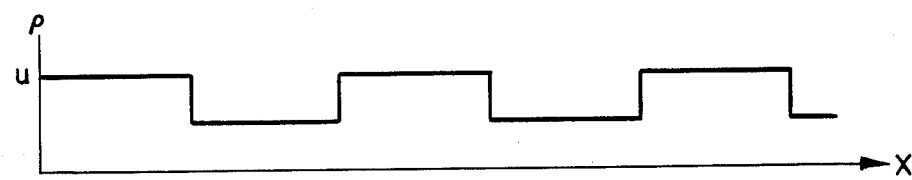
FIGS. 6a and 6b are diagrams of an object and three corrections to set regions above the upper bound of density to the upper bound, and regions outside the boundary and which have negative density to zero.
Figure 6B:
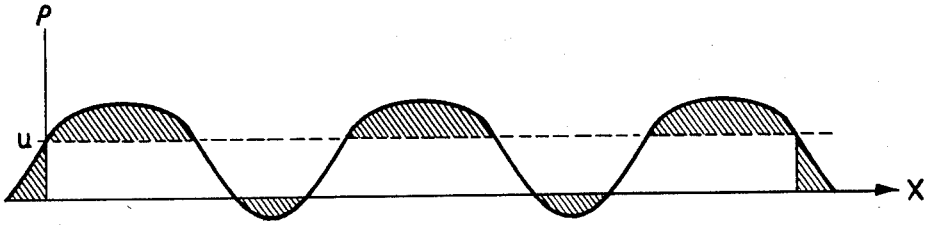

The three kinds of distortions produced in an object due to missing frequency components that have been discussed are illustrated pictorially in FIG. 6b. These distortions are that there are regions outside the boundary of the real object, some computed density values are higher than the upper bound u, and some computed density values are negative. The shape of the original object $\rho(x,y)$ in real space is shown in FIG. 6a. The three corrections that are made by the limited-angle reconstruction algorithm with the three constraints are that regions outside the boundary are set to zero, regions with a density above the upper boundary are set to the upper bound, and negative regions are set to zero. This is done on a pixel-by-pixel basis. The result is a better estimate of the original object, which may be further improved through an iterative algorithm to be described later. By decomposing an object into the component substances the nonlinear constraints of upper-boundness and positivity are used more efficiently.

Figure 7:
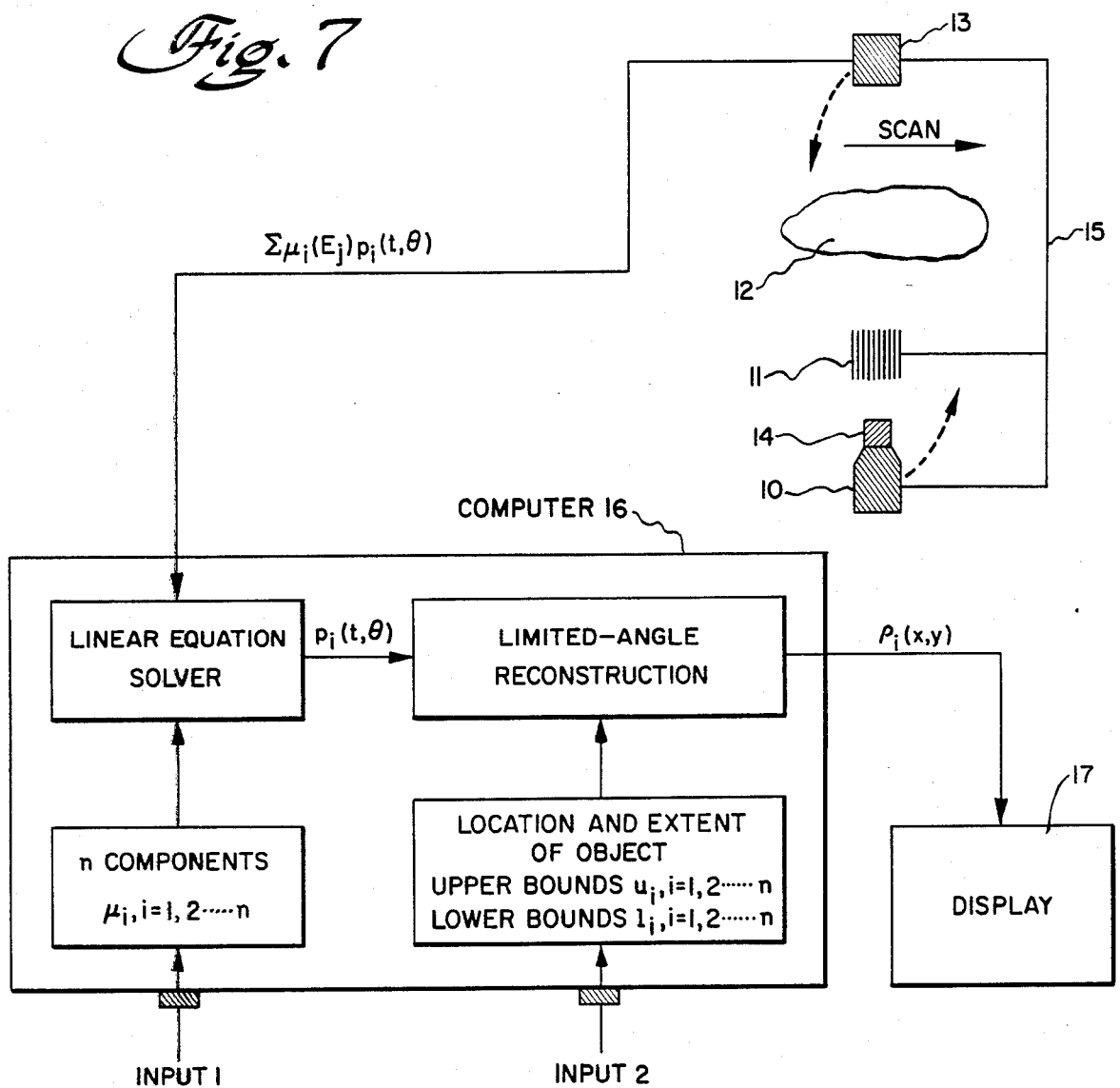
FIG. 7 is a diagram of one embodiment of the invention for industrial x-ray CT imaging.

FIG. 7 shows schematically one embodiment of the invention which is an industrial x-ray CT imager. An x-ray beam is generated by a source 10, collimated by a collimator 11 into parallel rays, passes through an object 12 and is detected by an x-ray detector 13. On the x-ray source is a device 14 for varying the energy of the x-ray beam; for example, it could be a filter in the path of the x-ray beam, or a knob for adjusting voltage on the x-ray tube. The source, collimator and detector are mounted on a yoke 15 and have linear movement to scan the object. Then the source 10, collimator 11, and detector 13 are rotated to change the scan angle and make a second linear scan, and so on. The object is scanned along many scan lines over the restricted angular range. The detected signals, which are given in equation system (1), are the projections $p(t,\theta,E_j)$ of the composite object in the limited angular range having different source energies $E_j$, and are fed into a computer 16. At input 1 of the computer are presented the following a priori information on the object: the number n of component substances contained in the composite object, and the attenuation coefficients $\mu_i(E_j)$ of each component i at different source energies $E_j$. With this information, the composite object projection data $p(t,\theta,E_j)$ can be decomposed by the linear equation solver, which computes the equation system (1), into the component substance projections $p_i(t,\theta)$. These are projections of each of the component substances over the limited angular range. At input 2 of the computer 16 are presented the following a priori information: location and extent of the object, and the upper bound $u_i$ and lower bound $l_i$ of each component substance. The lower bound is preferably that there are no negative densities. With this information the density $\rho_i(x,y)$ of each component substance can be reconstructed from its projections $p_i(t,\theta)$ in the limited angular range using a limited-angle reconstruction algorithm which works on this information.

One such reconstruction algorithm is the Fourier transform iteration algorithm proposed by the inventor, Perez-Mendez and Macdonald, in IEEE Transactions on Nuclear Science, NS-26 (1979) 2797–2805, the disclosure of which is incorporated herein by reference, to which is added the constraints if reconstructed $\rho_i(x,y)$ is $> u_i$ then reset to $u_i$, and if reconstructed $\rho_i(x,y)$ is negative then reset to zero. Another suitable algorithm is the Radon transform iteration algorithm given by the inventor and Perez-Mendez (citation above) to which the above two constraints are added. A third reconstruction algorithm is the iteration algorithm proposed by Lent and Tuy (above).

The output of the limited-angle reconstruction processing is the density distributions $\rho_i(x,y)$ of the component substances. This image data for the first component, second component, etc., is fed in sequence to the cathode ray tube or other display device 17 where the separately generated images are superimposed to produce the image of the composite object. The diamond-shaped object in FIG. 8 consists of three component substances which are a shell of density $\rho_1$, a center of density $\rho_2$, and a background or main body of density $\rho_3$. This was used as a simple computer simulated phantom to test the decomposition of an object into component substances in limited-angle reconstruction. At the display device 17 the three individually generated reconstructed images of the component substances are superimposed.

Figure 8:
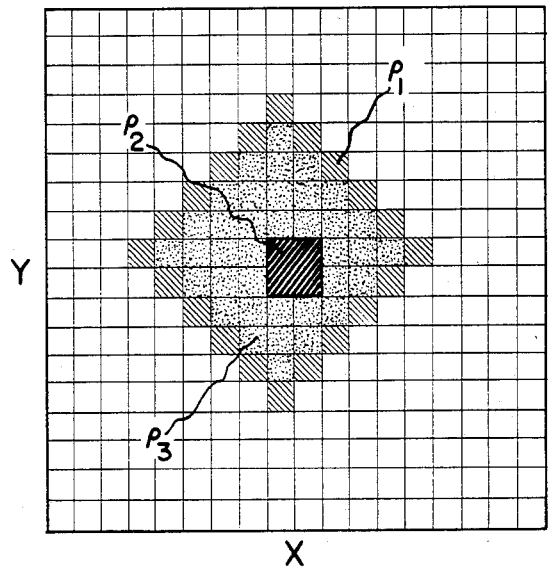
FIG. 8 illustrates a diamond shaped object having three component substances.

The effects of decomposing the composite object of FIG. 8 was studied in the ideal case of error free data. This is of course not a practical situation but indicates a theoretical limit to this kind of calculation. The allowed-cone frequency components of each component substance of the phantom were calculated from the component substance by direct Fourier transformation, and then used to recover the rest of the frequency components through the iteration algorithm shown in FIG. 9. This algorithm is an expansion of the one set forth by the inventor, Perez-Mendez, and Macdonald (above), to include the constraints of upper-boundness and positivity. Twenty interations were performed. The ratio of rms error to mean density of the reconstructed phantom were calculated and compared to the corresponding results obtained by reconstructing the phantom directly without going through decomposition. Decomposing the phantom brings about an improvement in all allowed-coned angles, but the improvement at large allowed-cone angles are especially impressive. Thus, decomposing an object in limited-angle reconstruction is more advantageous at large allowed-cone angles. This conclusion was verified by repeating the above reconstruction with the frequency components of each component substance calculated from its projections instead of from the component substance itself. FIG. 9 is a flow chart of a limited-angle reconstruction method, and is a Fourier transform iteration scheme for filling in the missing cone frequency components through the constraints of finite object extent, upper-boundness, and positivity. The missing cone components (see FIG. 3b) are set to zero initially. The estimated frequency spectrum of the object is transformed to the object-space using a Fast Fourier Transform (FFT) technique. The estimated object density is determined, corrected by resetting to zero those pixels outside the known extent of the object, resetting to the upper bound those pixels with density exceeding the upper bound, and resetting to zero those pixels with negative density. A new Fourier spectrum is calculated from the estimated object density using a FFT algorithm, and is corrected to the known frequency components inside the allowed-cone. The object is Fourier transformed back and forth between the object space and the Fourier space, being corrected in each instance by the known frequency components in the allowed-cone, the known finite extent of the object, and the constraints of upper-boundness and positivity.

In the foregoing discussion, it is assumed that a monoenergetic or monochromatic imaging agent is used. If this is not the case, as in x-ray imagings where panchromatic x-ray sources are employed, the attenuation coefficients $\mu_i(E_j)$ in equation system (1) should be taken to be the weighted average of the attenuation coefficients in the energy spectrum, which is the practice in current CT imaging.

Besides x-ray imaging, this method of reconstructing composite objects from the limited-angle information can be applied to any modality in which the projection images of different substances in an object change in different ways under change in the frequency or energy of the imaging agent. Some of these modalities are electron microscopy, ultrasound imaging, and neutron imaging. Summarizing, the method of limited-angle tomographic reconstruction for radiation imaging comprises the steps of: scanning the composite object at many angles over a restricted angular range using an imaging agent at different energies (the minimum number of energy levels is equal to the number of component substances); generating detected signals which are projections of the composite object in the limited angular range at the different energies; decomposing the composite object projections into projections of the individual component substances; producing a reconstructed image of each component substance from its projections and a priori information on the object; and superimposing the reconstructed images of the substances to yield a reconstruction of the composite object.

Further information is given in the paper "Improving the Accuracy of Limited-Angle Reconstruction by Multispectral Imaging" presented at the VIIth International Conference on Information Processing in Medical Imaging, Standford University, June 22-26, 1981 (to appear in the Conference Proceedings); and in the paper "The Use of Multispectral Imaging in Limited-Angle Reconstruction", IEEE Nuclear Science Symposium, San Francisco, Oct. 21-23, 1981 (published in IEEE Transactions on Nuclear Science, NS-29, February 1982, pp. 512-515).

While the invention has been particularly shown and described with reference to preferred embodiments thereof, it will be understood by those skilled in the art that the foregoing and other changes in form and details may be made therein without departing from the spirit and scope of the invention.

The invention claimed is:

1. A method of limited-angle tomographic reconstruction for radiation imaging of composite objects composed of at least two component substances, said method comprising the steps of:
   scanning the composite object at many scan angles over a limited angular range using an imaging agent at different energies, where the number of energies is at least equal to the number of component substances;
   generating detected signals which are projections of the composite object in the limited angular range at the different energies;
   decomposing said composite object projections into projections of each component substance;
   producing a reconstructed image of each component substance from its projections and known physical parameters of the object and substances, which are the finite extent of the composite object, the upper bound of the density of each component substance, and that there are no negative densities, the latter two being nonlinear constraints; and
   superimposing said reconstructed images to yield a tomographic reconstruction of the composite object.

2. The method of claim 1 wherein said reconstructed image of each component substance is produced by using a limited-angle reconstruction algorithm and resetting to zero those pixels outside the known extent of the composite object, resetting to the upper bound those pixels with density exceeding the upper bound, and resetting to zero those pixels with negative density.

3. A method of limited-angle tomographic reconstruction for x-ray imaging of composite objects composed of at least two component substances, said method comprising the steps of:
   taking multiple scans of the composite object at many scan angles over a limited angular range using x-rays at different energies, where the number of energies is equal to or greater than the number of component substances and the attenuation coefficients of the component substances are different;
   generating detected signals which are projections of the composite object in the limited angular range at the different energies;
   decomposing said composite object projections into projections of each component substance;
   producing the density distribution and a reconstructed image of each component substance from its last-mentioned projections and a priori information on the object and substances, which are the extent and location of the object, the upper bound of the densities of the component substances, and that there are no negative densities, the latter two being nonlinear constraints; and
   superimposing said reconstructed images to yield at tomographic reconstruction of the composite object.

4. The method of claim 3 wherein said reconstructed image of each component substance is produced by using a limited-angle algorithm such as Fourier transform iteration algorithm and resetting to zero those pixels outside the known extent of the composite object, resetting to the upper bound those pixels with density exceeding the upper bound, and resetting to zero those pixels with negative density.

* * * * *